United States Patent
Gu et al.

(10) Patent No.: US 12,359,024 B2
(45) Date of Patent: Jul. 15, 2025

(54) BIOMASS BENZOXAZINE-BASED SHAPE MEMORY RESIN, PREPARATION METHOD THEREFOR, AND APPLICATION THEREOF

(71) Applicant: SOOCHOW UNIVERSITY, Suzhou (CN)

(72) Inventors: Aijuan Gu, Suzhou (CN); Guozheng Liang, Suzhou (CN); Li Yuan, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 508 days.

(21) Appl. No.: 17/927,085

(22) PCT Filed: Sep. 29, 2020

(86) PCT No.: PCT/CN2020/119094
§ 371 (c)(1),
(2) Date: Nov. 22, 2022

(87) PCT Pub. No.: WO2021/238004
PCT Pub. Date: Dec. 2, 2021

(65) Prior Publication Data
US 2023/0242707 A1    Aug. 3, 2023

(30) Foreign Application Priority Data

May 23, 2020  (CN) .......................... 202010444854.4

(51) Int. Cl.
*C08G 73/02*   (2006.01)
*C07D 265/14*  (2006.01)

(52) U.S. Cl.
CPC ....... C08G 73/0233 (2013.01); C07D 265/14 (2013.01); *C08G 2280/00* (2013.01)

(58) Field of Classification Search
CPC ............ C08G 73/0233; C08G 2280/00; C08G 73/00; C08G 73/06; C07D 265/14
See application file for complete search history.

(56) References Cited

U.S. PATENT DOCUMENTS 10,501,578 B1 * 12/2019 Hreha .................. C07D 307/34

FOREIGN PATENT DOCUMENTS

| CA | 2167503 A1 | 11/1995 |
| CN | 105111438 A | 12/2015 |
| CN | 107459512 A | 12/2017 |
| CN | 111423580 A | 7/2020 |

OTHER PUBLICATIONS

Liu, et al., "Shape memory polybenzoxazines based on polyetheramine", Reactive and Functional Polymers, 102, 62-69, Mar. 11, 2016. (Year: 2016).*
Huang, Jinbai, "Preparation and Properties of Shape Memory Benzoxazines Based on Polyetheramine", A Dissertion for the Degree of M. Engineering, Hebei University, Mar. 15, 2017 (Mar. 15, 2017), ISSN: 1674-0246, pp. 2 and 7-9.
N. K. Sini et al. Renewable benzoxazine monomer from Vanillin: Synthesis, characterization, and studies on curing behavior, Journal of Polymer Science, Part A . . . Polymer Chemistry, vol. 52, No. 1, Nov. 6, 2013 (Nov. 6, 2013).

* cited by examiner

*Primary Examiner* — Christopher M Rodd
(74) *Attorney, Agent, or Firm* — SZDC Law PC

(57) ABSTRACT

A biomass benzoxazine-based shape memory resin, a preparation method therefor, and an application thereof. The method includes: using biomass furfuryl amine, vanillic aldehyde, and paraformaldehyde as raw materials; obtaining an aldehyde group-containing biomass benzoxazine monomer by means of a heating reaction; mixing the aldehyde group-containing biomass benzoxazine monomer with polyether amine, and obtaining a Schiff base biomass benzoxazine monomer by means of a coupling reaction; and curing the Schiff base biomass benzoxazine monomer to obtain the biomass benzoxazine resin having a shape memory function. The benzoxazine-based shape memory resin has excellent thermal performance, high tensile modulus, high strength; an original shape can be permanently changed according to needs, the defect that traditional cross-linked polymers cannot be reprocessed after being formed is overcome, a recovery function under the condition of heating stimulation achieved, an application range of a shape memory polymer widened due to excellent thermal performance and mechanical performance.

10 Claims, 4 Drawing Sheets

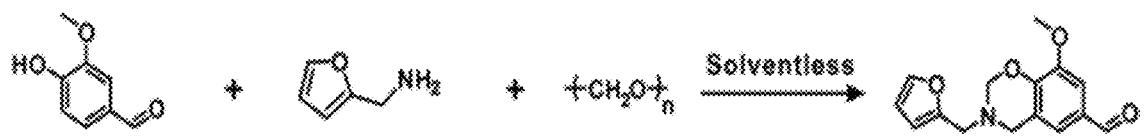
*FIG. 1*
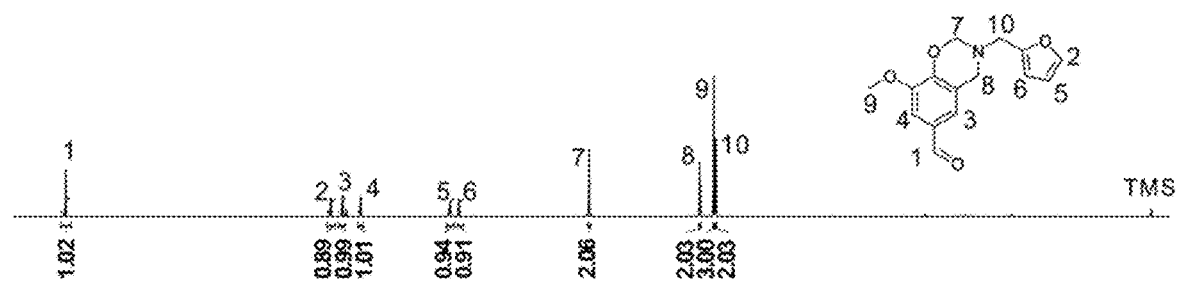
*FIG. 2*
*FIG. 3*
*FIG. 4*
*FIG. 5*

BIOMASS BENZOXAZINE-BASED SHAPE MEMORY RESIN, PREPARATION METHOD THEREFOR, AND APPLICATION THEREOF

This application is the National Stage Application of PCT/CN2020/119094, filed on Sep. 29, 2020, which claims priority to Chinese Patent Application No. 202010444854.4, filed on May 23, 2020, which is incorporated by reference for all purposes as if fully set forth herein.

TECHNICAL FIELD

The present invention relates to a shape memory bio-based benzoxazine resin, and preparation and application thereof, in particular, to a shape memory bio-based benzoxazine resin, and preparation and application method thereof, belonging to the technical field of functional polymer materials.

TECHNICAL BACKGROUND

Shape memory polymers (SMPs) are a kind of stimulus-response polymers. They can change and fix shape under certain condition; after that, the original shape will be recovered through the external stimulation such as heat, electricity, light, chemical induction, etc.

Aerospace, electronics, medical devices, robotics, information, architecture, textiles and daily necessities; especially when they are used as deployment components and structures, and then complex, large-scale and large-volume assembly of equipment will be achieved, and thus greatly promoting the progress of many industries.

High performance and greenization are the trends of material's research and development, the same is true for the development of SMPs. High heat-resistance and high mechanical strength are typical indexes of high performance polymers, however, most SMPs developed so far have low glass transition temperature (Tg), thus cannot be applied in aerospace and other fields that require high heat-resistance. On the other hand, developing the solvent-free strategy and using bio-based polymers are important methods to realize the greenization of materials, but few studies on green preparation of SMPs have been reported.

Benzoxazine resin is a typical heat-resistant thermosetting resin, it not only has the advantages of high Tg, high storage modulus and nearly zero shrinkage during the curing process, but also has strong ability of structure modification through designing different raw materials (phenol and amine) to get resins with different performance. These inherent advantages of benzoxazine resins provide the basic merits for preparing high performance SMPs. However, up-to date, available neat benzoxazine resins tend to be brittle, while only four of them have shape memory properties. To achieve shape memory performance, researchers copolymerized benzoxazine resin with other resins, but all of them were not bio-based resins and their Tg values were not higher than 170° C. Briefly speaking, no bio-based benzoxazine resins have shape memory properties.

Therefore, developing new bio-based benzoxazine resins with shape memory properties and high Tg through a solvent-free strategy is a valuable and interesting topic. Our research reported herein has two targets, one is building a green solvent-free strategy to synthesize high performance bio-based benzoxazine monomer, and the other is developing shape memory bio-based benzoxazine resin with high thermal and mechanical properties.

In the sum, the prior art has made great progress in the research and development of shape memory polymers. However, building a green solvent-free strategy to high heat resistance, high tensile modulus and strength of shape memory bio-based benzoxazine resin still has certain challenges.

Technical Problem

The object of the present invention is to provide a high heat resistance, high tensile modulus and strength of shape memory bio-based benzoxazine resin, and preparation and application thereof.

Technical Solutions

In order to achieve the above-mentioned object of the invention, the technical solution adopted by the present invention is:

A shape memory bio-based benzoxazine resin, which the preparation method includes the following steps:

(1) The mixture of furfurylamine, formaldehyde compound and vanillin is heated and reacted and then recrystallized to obtain bio-based benzoxazine monomer containing aldehyde group;

(2) Through coupling reaction between bio-based benzoxazine monomer containing aldehyde group and polyetheramine to obtain Schiff base benzoxazine monomer;

(3) The Schiff base benzoxazine monomer is cured to obtain a shape memory bio-based benzoxazine resin.

In step (1) of the present invention, adding vanillin into the mixture of furfurylamine and formaldehyde compound after stirring at room temperature; the formaldehyde compound is formaldehyde and/or paraformaldehyde; the molar ratio of furfurylamine, formaldehyde compound and vanillin is 100:(200-220):100; the temperature of the heating reaction ranges from 80° C. to 90° C., and the reaction time ranges from 4 h to 6 h, and recrystallized with ethanol.

In step (2) of the present invention, coupling reaction without using any solvent in both synthesis and purification processes; the temperature of coupling reaction ranges from 125° C. to 130° C., the reaction time ranges from 1 h to 2 h; the molar ratio of bio-based benzoxazine monomer containing aldehyde group and polyetheramine is 100:50.

In step (3) of the present invention, the Schiff base benzoxazine monomer is degassed and then cured; the temperature of curing ranges from 150° C. to 240° C., time ranges from 10 h to 24 h. Preferably, in step (3), the curing is a stepped heating method, the holding time at each step temperature is not less than 1 h, and the temperature difference between adjacent steps is not more than 30° C.

Specifically, the preparation of shape memory bio-based benzoxazine resin is as follows:

(1) By molar parts, mixing 100 parts of furfurylamine and ranges from 200 to 220 parts of formaldehyde at room temperature with 15 min-stirring, followed by adding 100 parts of vanillin to get a mixture. The mixture is heated to ranges from 80° C. to 90° C. with time ranges from 4 h to 6 h stirring and reacting. After that the mixture is cooled to room temperature to get a crude product, which is then recrystallized with ethanol. And dried the obtained product is bio-based benzoxazine monomer containing aldehyde group.

(2) By molar parts, mixing 100 parts of bio-based benzoxazine monomer containing aldehyde group and 50 parts of polyetheramine (D-230), reacting time ranges from 1 h to 2 h at temperature ranges from 125° C. to 130° C. After that the mixture is cooled to room temperature, drying, to obtain Schiff base benzoxazine monomer.

(3) The Schiff base benzoxazine monomer obtained in step (2) is degassed and cured to obtain a shape memory bio-based benzoxazine resin.

The present invention discloses the application of shape memory bio-based benzoxazine resin in the preparation of shape memory materials. Especially, shape memory bio-based benzoxazine resin has excellent deformation recovery performance. No need to copolymerize benzoxazine resin with other resins.

The present invention discloses the method for shape change and recovery of shape memory bio-based benzoxazine resin includes the following steps:

(1) At the deformation temperature, bending the original shape memory bio-based benzoxazine resin into a temporary shape; followed by quickly dropping to room temperature to keep the shape;

(2) Go on heating the new shape memory bio-based benzoxazine resin at deformation temperature, and new shape memory bio-based benzoxazine resin is recovered to the original shape, completing a shape memory cycle.

In the above technical solution, in step (1), the heating temperature ranges from 290° C. to 300° C., time the ranges from 20 s to 30 s; when the deformation temperature reaching the ranges from Tg+10° C. to Tg+20° C. of shape memory bio-based benzoxazine resin.

Specifically, the method for shape change and recovery of shape memory bio-based benzoxazine resin includes the following steps:

(1) When the temperature reaching the ranges from Tg+10° C. to Tg+20° C., the original shape polymer system is bent into the required temporary shape with external force and then continue heating to range from 290° C. to 300° C. and maintain at this temperature and external force, so that eversible exchange reaction of the Schiff base dynamic bond in the polymer system.

(2) Dropping to room temperature, the new shape described in step (1) is fixed and becomes a new permanent shape II of the shape memory bio-based benzoxazine resin.

(3) Heating a new permanent shape II of the shape memory bio-based benzoxazine resin to the ranges from Tg+10° C. to Tg+20° C., the cross-linked polymer will automatically from the permanent shape II in step (2) return to permanent shape I (the original shape).

Beneficial Effect

Compared with the prior art, the beneficial effects of the present invention are as follows:

1. The present invention synthesis of Schiff base benzoxazine monomer using furfurylamine and vanillin as raw materials, these are green bio-based raw material.

2. A shape memory bio-based benzoxazine resin prepared by the present invention has outstanding heat resistance, Tg is 280° C., and has high storage modulus (2.40 GPa), tensile strength (90.4 MPa). Thus provides a reliable basis for its application in cutting-edge fields. The high heat resistance of the resin benefits from the involvement of furan in the resin in cross-linked and the large number of hydrogen bonding in the cross-linked network, and its excellent mechanics. The performance is due to the combination of the rigid benzoxazine structure and the flexible polyetheramine structure in the cross-linked network.

3. The thermosetting shape memory bio-based benzoxazine resin prepared by the present invention has the advantage of being able to change its initial shape, so that the crosslinking network can be reconstructed, thereby obtaining a stable permanent shape. This application method overcomes the defect that traditional cross-linked polymers cannot be processed again after molding, and the shape recovery rate of the prepared biomass benzoxazine-based shape memory resin is as high as 98%.

4. A shape memory bio-based benzoxazine resin prepared by the present invention adopts a solvent-free strategy, which is green and environmentally friendly, has a simple preparation process, avoids the use of a large amount of solvents in the preparation process, and is easy to industrialized large-scale production; at the same time, the preparation method prepared by the present invention is based on When the shape memory resin of biomass benzoxazine is applied, the original shape can be permanently changed as required, which overcomes the defect that the traditional cross-linked polymer cannot be processed again after molding, and saves the processing cost of the original structure.

DESCRIPTION OF THE DRAWINGS

FIG. 1 shows synthesis route of bio-based benzoxazine monomer containing aldehyde group in Example 1.

FIG. 2 shows $^1$H NMR of bio-based benzoxazine monomer containing aldehyde group in Example 1.

FIG. 3 shows $^{13}$C NMR of bio-based benzoxazine monomer containing aldehyde group in Example 1.

FIG. 4 shows synthesis route of Schiff base benzoxazine monomer in Example 1.

FIG. 5 shows $^1$H NMR of Schiff base benzoxazine monomer in Example 1.

EXAMPLES OF THE PRESENT INVENTION

The present invention disclosed a shape memory bio-based benzoxazine resin, which the preparation method including the following steps:

(1) The mixture of furfurylamine, formaldehyde compound and vanillin is heated and reacted and then recrystallized to obtain bio-based benzoxazine monomer containing aldehyde group;

(2) Through coupling reaction between bio-based benzoxazine monomer containing aldehyde group and polyetheramine to obtain Schiff base benzoxazine monomer;

(3) The Schiff base benzoxazine monomer is cured to obtain a shape memory bio-based benzoxazine resin.

Figure 10:
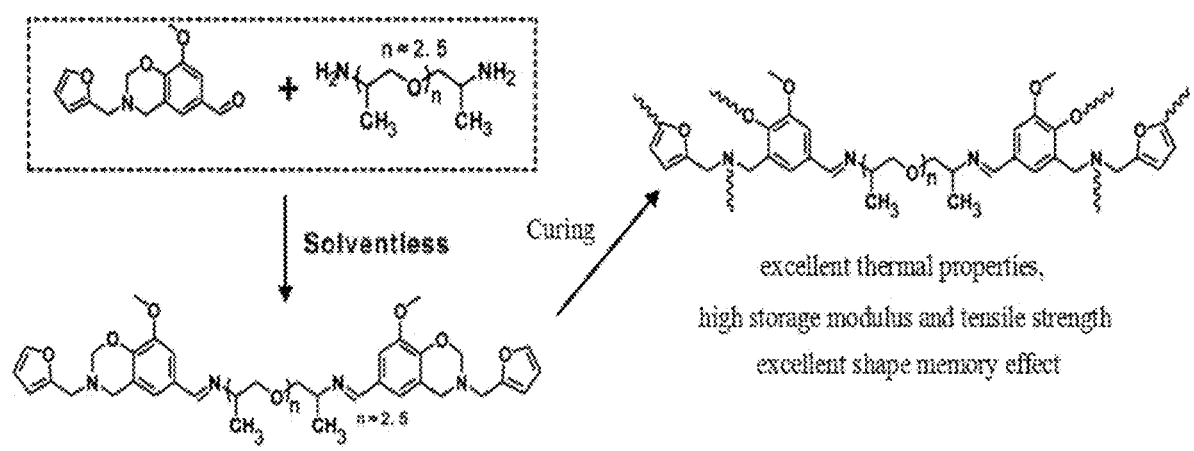
FIG. 10 shows schematic diagram of preparation of shape memory resin bio-based benzoxazine in the present invention.

The schematic diagram was referred to FIG. 10.

The technical scheme of the present invention is further elaborated in combination with attached Figures and Examples. All raw materials are commercially available, and the test methods involved are conventional test methods in the field.

Example 1

(1) Synthesis of Bio-Based Benzoxazine Monomer Containing Aldehyde Group

Furfurylamine (9.71 g) and polyformaldehyde (6.00 g, CAS #: 30525-89-4) at room temperature with 15 min-stirring, followed by adding vanillin (15.22 g) to get a mixture. The mixture was heated to 85° C. and maintained at this temperature for 5 h. After that the mixture was cooled to room temperature to get a crude product, which was then recrystallized with ethanol. After the resulting pure product was dried was bio-based benzoxazine monomer containing aldehyde group.

In this Example, synthesis route, $^1$H NMR and $^{13}$C NMR of bio-based benzoxazine monomer containing aldehyde group were referred to FIG. 1, FIG. 2 and FIG. 3, respectively.

Saw FIG. 2, it is $^1$H NMR of bio-based benzoxazine monomer containing aldehyde group. The sharp unimodal peak at about 9.81 ppm is active hydrogen on the aldehyde group in benzoxazine monomer, at the same time, the characteristic peaks in oxazine ring appear at 5.08 ppm and 4.09 ppm. Above spectra of bio-based benzoxazine monomer containing aldehyde group demonstrate the successful synthesis of bio-based benzoxazine monomer containing aldehyde group.

Saw FIG. 3, it is $^{13}$C NMR of bio-based benzoxazine monomer containing aldehyde group. the characteristic peaks of aldehyde group in benzoxazine monomer at about 190.8 ppm, at the same time, the characteristic peaks in oxazine ring appear at 83.3 ppm and 56.0 ppm.

(2) Synthesis of Schiff Base Benzoxazine Monomer

Bio-based benzoxazine monomer containing aldehyde group (27.31 g) and PEA D-230 (11.5 g, molecular weight is 230), were heated to 125° C. and stirred at this temperature for 1 h, after that the mixture was cooled to room temperature, the product was dried to obtain Schiff base benzoxazine monomer.

It can be seen from synthesis route of Schiff base benzoxazine monomer provided of Example 1 in FIG. 4, that the reaction is coupling reaction.

Saw FIG. 5, it is $^1$H NMR of Schiff base benzoxazine monomer. The sharp unimodal peak at about 8.15 ppm is active hydrogen on the aldehyde group, the characteristic peaks in oxazine ring appear at 5.01 ppm and 4.02 ppm. It demonstrated the successful synthesis of Schiff base benzoxazine monomer.

(3) Preparation of Benzoxazine Resin

The Schiff base benzoxazine monomer (10.0 g) was heated and degassed under vacuum at 150° C. for 10 min, and then the molten liquid was cured using the program of 160° C./2 h+180° C./2 h+200° C./2 h+220° C./2 h+240° C./2 h, the resulting cured resin was coded as shape memory bio-based benzoxazine resin.

Figure 6:
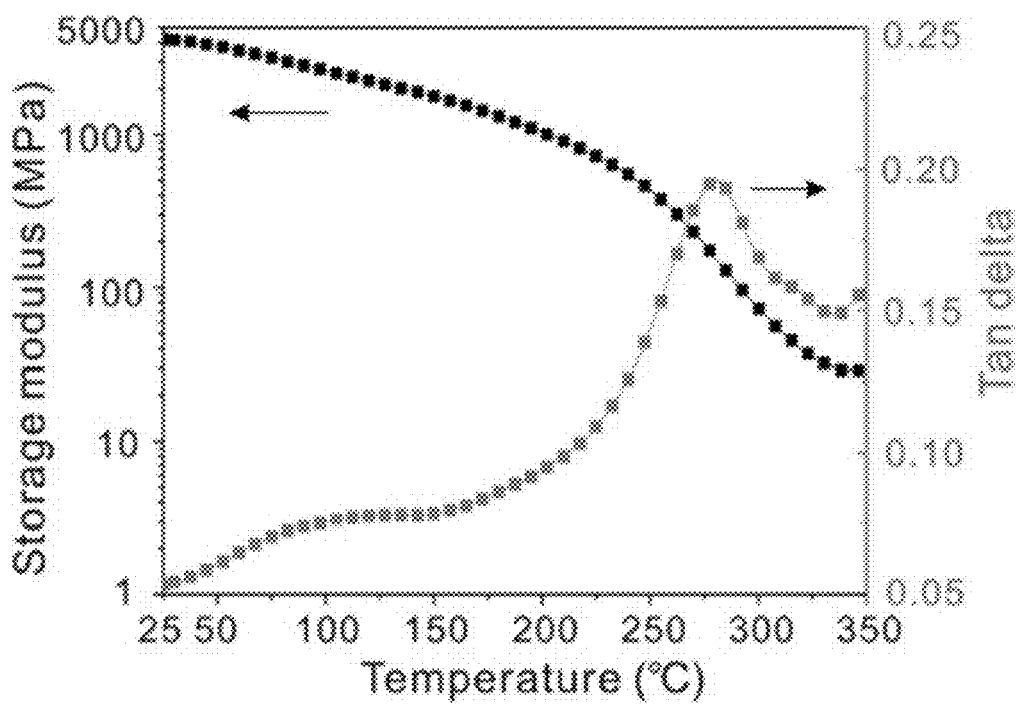
FIG. 6 shows the FTIR spectrum of Schiff base benzoxazine monomer and the cured product in Example 1.
Figure 7:
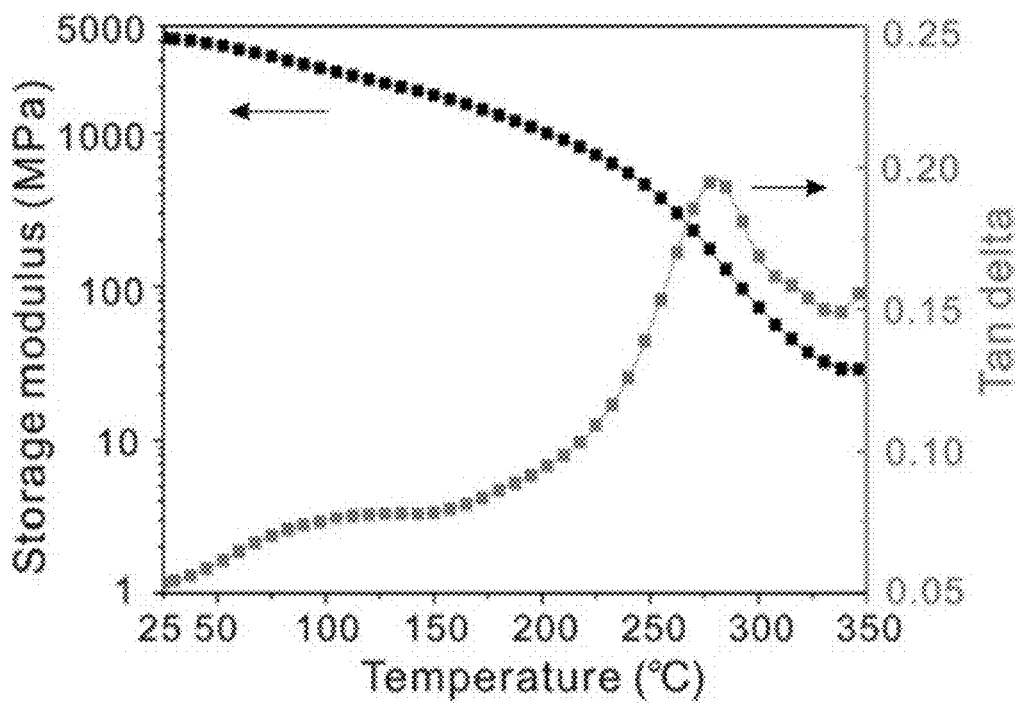
FIG. 7 shows DMA curve of shape memory resin bio-based benzoxazine prepared in Example 1.
Figure 8:
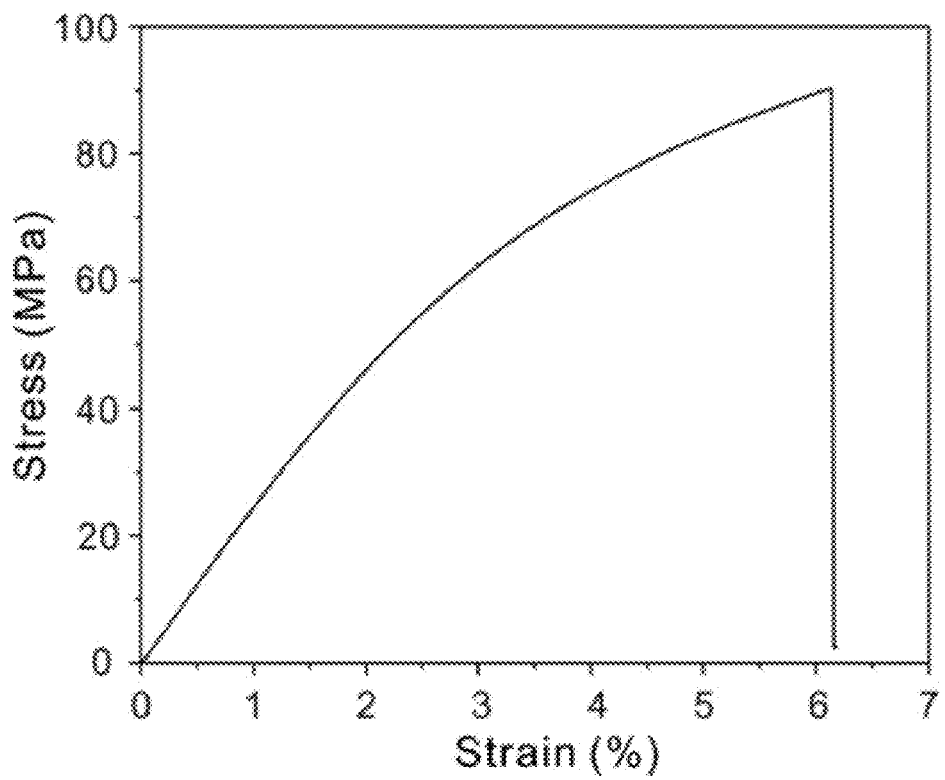
FIG. 8 shows the stress-strain curve of shape memory resin bio-based benzoxazine prepared in Example 1.

In this Example, the FTIR spectrum, DMA curve, the stress-strain curve of shape memory bio-based benzoxazine resin were referred to FIG. 6, FIG. 7 and FIG. 8 respectively.

From FTIR spectra of FIG. 6, it can be seen that both spectra show the asymmetric vibration peak of C—O—C group (1288 $cm^{-1}$ and 3331 $cm^{-1}$) in the oxazine ring mode and out-of-the-plane vibration of C—H (914 $cm^{-1}$), primarily proving that the formation of a cross-linked network.

As shown in FIG. 7, it is DMA curve of shape memory resin bio-based benzoxazine. It can be seen that the thermosetting shape memory resin bio-based benzoxazine prepared in Example 1 has a storage modulus of 4.20 GPa at 25° C. Its glass transition temperature (Tg) is 280° C., which proves that shape memory resin bio-based benzoxazine prepared by the present invention has outstanding heat resistance.

In the prior art, $T_g$ (DMA) of benzoxazine resins reported early was 100° C., the highest $T_g$ (DMA) of poly (VFA-atpe) is 167° C. Saw Jinbai Huang's M. S. thesis "synthesis and properties of Shape memory polybenzoxazines based on polyetheramine", $T_g$ (DMA) of benzoxazine resins reported ranged from 40 to 91° C.; Xuehui Su's M. S. thesis, $T_g$ (DMA) of benzoxazine resins reported ranged from 68 to 123° C.; Cuiyun Li's M. S. thesis, $T_g$ (DMA) of benzoxazine resins reported ranged from 33 to 167° C. CN105111438A discloses a polyetheramine benzoxazine, which has good heat resistance but does not have shape memory and cannot change the original shape to a fixed new shape after heating.

The benzoxazine prepared in the technology disclosed above is prepared based on the Mannich reaction of petroleum-based phenol and polyetheramine as two raw materials. The final prepared benzoxazine without shape memory properties and high Tg. At the same time, the synthetic method of benzoxazine in the above disclosed technology is not a general synthetic method. In related work, the applicant replaced the petroleum-based phenolic raw material with the bio-based raw material vanillin, using solvent and solvent-free materials respectively. A total of three methods to prepare polyetheramine backbone benzoxazine monomers failed to obtain the target product. The reason is that the aldehyde group in vanillin reacts preferentially with polyetheramine to form Schiff base. The benzoxazine monomer cannot be prepared by Mannich reaction. The specific operation is as follows:

Method 1: Mixed 1.52 g vanillin, 1.15 g polyetheramine D-230 (molecular weight 230) and 0.6 g paraformaldehyde, reacted for 4 h, 5 h or 6 h at 85° C. respectively, after that the mixture was cooled to room temperature e to get a crude product, which was washed three times with 20 mL 1N NaOH solution after added 20 mL chloroform (to remove unreacted phenolic materials), collected the organic layer, dried with sodium sulphate anhydrous and evaporated, but no product was obtained.

Method 2: Added 1.52 g vanillin, 1.15 g polyetheramine D-230 (molecular weight 230) and 0.6 g paraformaldehyde to 20 mL chloroform, reacted at reflux temperature for 4 h, 5 h or 6 h respectively, after that the mixture was cooled to room temperature e to get a crude product, which was washed three times with 20 mL 1N NaOH solution (to remove unreacted phenolic materials), and the organic layer was collected and dried with anhydrous sodium sulfate. The solvent was evaporated and no product was obtained.

Method 3: Added 1.52 g vanillin, 1.15 g polyetheramine D-230 (molecular weight 230) and 0.6 g paraformaldehyde to 20 mL ethanol, reacted at reflux temperature for 4 h, 5 h or 6 h respectively, evaporation the solvent, added 20 mL chloroform, which was washed three times with 20 mL 1N NaOH solution (to remove unreacted phenolic materials), and the organic layer was collected and dried with anhydrous sodium sulfate. The solvent was evaporated and no product was obtained.

Through the above synthesis experiments and the summary of the performances of the benzoxazine resin synthesized from polyetheramine as the raw material disclosed in the prior art, it is known that the raw material formulation and synthesis technology disclosed in the prior art are not suitable for the preparation of high heat resistance Shape memory benzoxazine resin. In this application, a two-step synthesis method is innovatively used: firstly, vanillin and furfurylamine are mixed to obtain benzoxazine monomer containing aldehyde group. The furan of furfurylamine was participated in crosslinked network during thermal curing. Thereby increases the heat resistance of the resin. Secondly, the public technology, polyetheramine is used as a coupling reaction raw material instead of Mannich reaction raw material, and the prepared Schiff base type benzoxazine monomer contains both rigid segments and tough polyether chains.

It laid a foundation for the preparation of shape memory benzoxazine resin with high heat resistance. The invention obviously provides a new technical idea, develops a new Schiff bio-based benzoxazine monomer, and obtains a product with excellent heat resistance and shape memory performance.

FIG. 8 shows the stress-strain curve of shape memory resin bio-based benzoxazine. It can be seen that tensile strengths is 90.4 MPa, storage modulus is 2.46 GPa, and proves that the shape memory resin bio-based benzoxazine prepared by the present invention has outstanding mechanical properties.

(4) The application method of the shape memory resin bio-based benzoxazine: the sample was heated to 300° C. (Tg+20° C.), was bent into the required temporary shape with external force, and then continue heating to 300° C. and maintain at this temperature and external force, so that eversible exchange reaction of the Schiff base dynamic bond in the polymer system. Dropping to room temperature, the new shape; after that, the sample was placed in a hot air atmosphere Heating the new permanent shape of the shape memory bio-based benzoxazine resin to Tg+20° C., and maintain for 40 s the cross-linked polymer will automatically return to the original shape.

Figure 9:
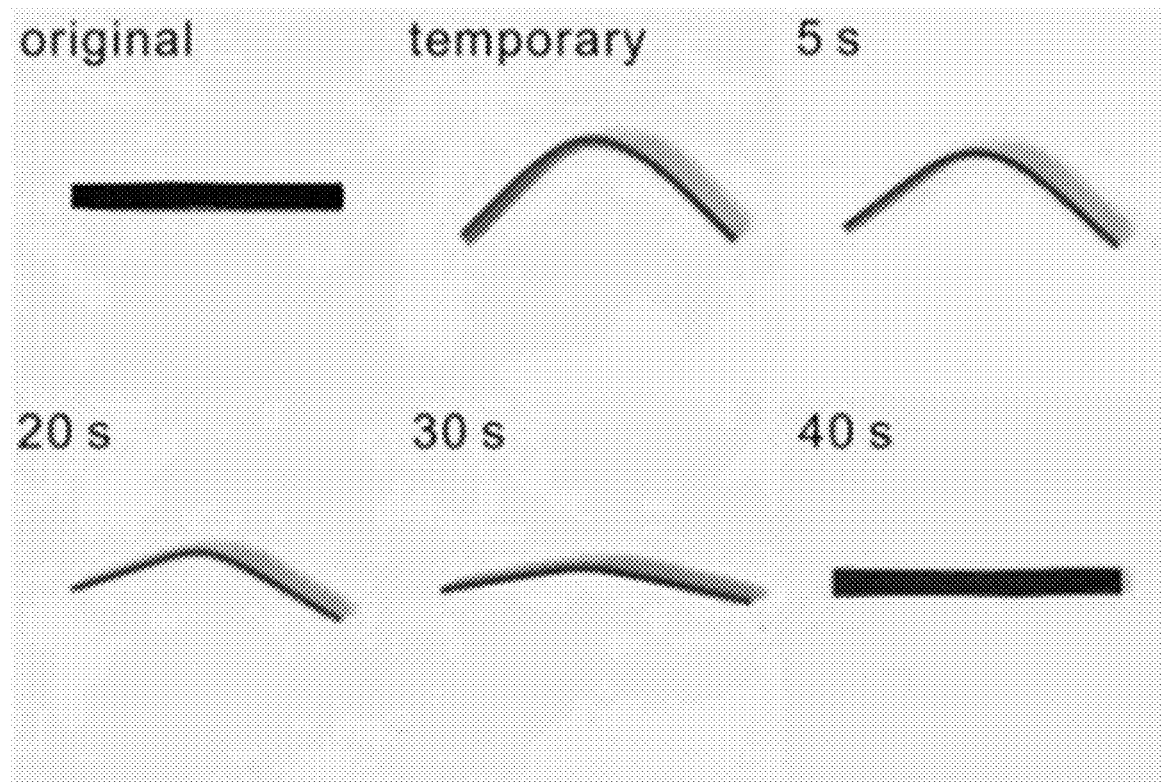
FIG. 9 shows shape memory effect of shape memory resin bio-based benzoxazine prepared in Example 1.

FIG. 9 shows shape memory effect of shape memory resin bio-based benzoxazine. According to the deformation angle that the recovery efficiency of shape memory resin bio-based benzoxazine prepared in Example 1 was calculated to be 98%, which proves that the shape memory resin prepared by the present invention has outstanding shape memory performance.

According to above method, If the new shape is designed into other shapes such as a circle shape and an S shape, and the recovery efficiency of shape memory resin bio-based benzoxazine reaches more than 96%.

If adjusted the reaction time to 0.5 h of step (2) in Example 1 the Tg (DMA) of shape memory resin bio-based benzoxazine was 241° C.

If adjusted the reaction time to 3 h of step (2) in Example 1 the Tg (DMA) of shape memory resin bio-based benzoxazine was 259° C.

Cured the bio-based benzoxazine monomer containing aldehyde group prepared by step (1) according to step (3), and the obtained resin had no shape memory effect.

Example 2

(1) Synthesis of Bio-Based Benzoxazine Monomer Containing Aldehyde Group

Furfurylamine (9.71 g) and polyformaldehyde (12.65 g CAS #: 30525-89-4) at room temperature with 15 min-stirring, followed by adding vanillin (15.22 g) to get a mixture. The mixture was heated to 85° C. and maintained at this temperature for 5 h. After that the mixture was cooled to room temperature to get a crude product, which was then recrystallized with ethanol. After the resulting pure product was dried was bio-based benzoxazine monomer containing aldehyde group.

(2) Synthesis of Schiff Base Benzoxazine Monomer

Bio-based benzoxazine monomer containing aldehyde group (30.0 4 g) and PEA D-230 (12.65 g molecular weight is 230), were heated to 125° C. and stirred at this temperature for 1.5 h, after that the mixture was cooled to room temperature, the product was dried to obtain Schiff base benzoxazine monomer.

(3) Preparation of Benzoxazine Resin

The Schiff base benzoxazine monomer (11.0 g) was heated and degassed under vacuum at 150° C. for 10 min, and then the molten liquid was cured using the program of 160° C./2 h+180° C./2 h+200° C./2 h+220° C./2 h+240° C./2 h, the resulting cured resin was coded as shape memory bio-based benzoxazine resin.

(4) The application method of the shape memory resin bio-based benzoxazine: the sample was heated to 300° C. (Tg+20° C.), was bent into the required temporary shape with external force, and then continue heating to 300° C. and maintain at this temperature and external force, so that eversible exchange reaction of the Schiff base dynamic bond in the polymer system. Dropping to room temperature, the new shape; after that, the sample was placed in a hot air atmosphere Heating the new permanent shape of the shape memory bio-based benzoxazine resin to Tg+20° C., and maintain for 40 s the cross-linked polymer will automatically return to the original shape.

Example 3

(1) Synthesis of Bio-Based Benzoxazine Monomer Containing Aldehyde Group

Mixed furfurylamine (9.71 g) and 40% formaldehyde aqueous solution (15 g) at room temperature with 15 min-stirring, followed by adding vanillin (15.22 g) to get a mixture. The mixture was heated to 85° C. and maintained at this temperature for 5 h. After that the mixture was cooled to room temperature to get a crude product, which was then recrystallized with ethanol. After the resulting pure product was dried was bio-based benzoxazine monomer containing aldehyde group.

(2) Synthesis of Schiff Base Benzoxazine Monomer

Bio-based benzoxazine monomer containing aldehyde group (27.31 g) and PEA D-230 (11.50 g molecular weight is 230), were heated to 125° C. and stirred at this temperature for 2 h, after that the mixture was cooled to room temperature, the product was dried to obtain Schiff base benzoxazine monomer.

(3) Preparation of Benzoxazine Resin

The Schiff base benzoxazine monomer (10.5 g) was heated and degassed under vacuum at 150° C. for 10 min, and then the molten liquid was cured using the program of 160° C./2 h+180° C./2 h+200° C./2 h+220° C./2 h+240° C./2 h, the resulting cured resin was coded as shape memory bio-based benzoxazine resin.

(4) The application method of the shape memory resin bio-based benzoxazine: the sample was heated to 300° C. (Tg+20° C.), was bent into the required temporary shape with external force, and then continue heating to 300° C. and maintain at this temperature and external force, so that eversible exchange reaction of the Schiff base dynamic bond in the polymer system. Dropping to room temperature, the new shape; after that, the sample was placed in a hot air atmosphere Heating the new permanent shape of the shape memory bio-based benzoxazine resin to Tg+20° C., and maintain for 40 s the cross-linked polymer will automatically return to the original shape.

Example 4

(1) Synthesis of Bio-Based Benzoxazine Monomer Containing Aldehyde Group

Furfurylamine (9.71 g) and polyformaldehyde (6.00 g) at room temperature with 15 min-stirring, followed by adding vanillin (15.22 g) to get a mixture. The mixture was heated to 80° C. and maintained at this temperature for 4 h. After that the mixture was cooled to room temperature to get a crude product, which was then recrystallized with ethanol. After the resulting pure product was dried was bio-based benzoxazine monomer containing aldehyde group.

(2) Synthesis of Schiff Base Benzoxazine Monomer

Bio-based benzoxazine monomer containing aldehyde group (32.77 g) and PEA D-230 (3.8 g, molecular weight is 230), were heated to 130° C. and stirred at this temperature for 1 h, after that the mixture was cooled to room temperature, the product was dried to obtain Schiff base benzoxazine monomer.

(3) Preparation of Benzoxazine Resin

The Schiff base benzoxazine monomer (11.0 g) was heated and degassed under vacuum at 150° C. for 10 min, and then the molten liquid was cured using the program of 160° C./2 h+180° C./2 h+200° C./2 h+220° C./2 h+240° C./2 h, the resulting cured resin was coded as shape memory bio-based benzoxazine resin.

(4) The application method of the shape memory resin bio-based benzoxazine: the sample was heated to 300° C. (Tg+20° C.), was bent into the required temporary shape with external force, and then continue heating to 300° C. and maintain at this temperature and external force, so that eversible exchange reaction of the Schiff base dynamic bond in the polymer system. Dropping to room temperature, the new shape; after that, the sample was placed in a hot air atmosphere Heating the new permanent shape of the shape memory bio-based benzoxazine resin to Tg+20° C., and maintain for 40 s the cross-linked polymer will automatically return to the original shape.

Example 5

(1) Synthesis of Bio-Based Benzoxazine Monomer Containing Aldehyde Group

Furfurylamine (9.71 g) and polyformaldehyde (6.00 g) at room temperature with 15 min-stirring, followed by adding vanillin (15.22 g) to get a mixture. The mixture was heated to 80° C. and maintained at this temperature for 5 h. After that the mixture was cooled to room temperature to get a crude product, which was then recrystallized with ethanol. After the resulting pure product was dried was bio-based benzoxazine monomer containing aldehyde group.

(2) Synthesis of Schiff Base Benzoxazine Monomer

Bio-based benzoxazine monomer containing aldehyde group (27.31 g) and PEA D-230 (11.50 g molecular weight is 230), were heated to 130° C. and stirred at this temperature for 1.5 h, after that the mixture was cooled to room temperature, the product was dried to obtain Schiff base benzoxazine monomer.

(3) Preparation of Benzoxazine Resin

The Schiff base benzoxazine monomer (11.0 g) was heated and degassed under vacuum at 150° C. for 10 min, and then the molten liquid was cured using the program of 160° C./2 h+180° C./2 h+200° C./2 h+220° C./2 h+240° C./2 h, the resulting cured resin was coded as shape memory bio-based benzoxazine resin.

(4) The application method of the shape memory resin bio-based benzoxazine: the sample was heated to 300° C. (Tg+20° C.), was bent into the required temporary shape with external force, and then continue heating to 300° C. and maintain at this temperature and external force, so that eversible exchange reaction of the Schiff base dynamic bond in the polymer system. Dropping to room temperature, the new shape; after that, the sample was placed in a hot air atmosphere Heating the new permanent shape of the shape memory bio-based benzoxazine resin to Tg+20° C., and maintain for 40 s the cross-linked polymer will automatically return to the original shape.

Example 6

(1) Synthesis of Bio-Based Benzoxazine Monomer Containing Aldehyde Group

Furfurylamine (9.71 g) and polyformaldehyde (6.00 g) at room temperature with 15 min-stirring, followed by adding vanillin (15.22 g) to get a mixture. The mixture was heated to 80° C. and maintained at this temperature for 6 h. After that the mixture was cooled to room temperature to get a crude product, which was then recrystallized with ethanol. After the resulting pure product was dried was bio-based benzoxazine monomer containing aldehyde group.

(2) Synthesis of Schiff Base Benzoxazine Monomer

Bio-based benzoxazine monomer containing aldehyde group (32.77 g) and PEA D-230 (13.8 g, molecular weight is 230), were heated to 130° C. and stirred at this temperature for 2 h, after that the mixture was cooled to room temperature, the product was dried to obtain Schiff base benzoxazine monomer.

(3) Preparation of Benzoxazine Resin

The Schiff base benzoxazine monomer (11.0 g) was heated and degassed under vacuum at 150° C. for 10 min, and then the molten liquid was cured using the program of 160° C./2 h+180° C./2 h+200° C./2 h+220° C./2 h+240° C./2 h, the resulting cured resin was coded as shape memory bio-based benzoxazine resin.

(4) The application method of the shape memory resin bio-based benzoxazine: the sample was heated to 300° C. (Tg+20° C.), was bent into the required temporary shape with external force, and then continue heating to 300° C. and maintain at this temperature and external force, so that eversible exchange reaction of the Schiff base dynamic bond in the polymer system. Dropping to room temperature, the new shape; after that, the sample was placed in a hot air atmosphere Heating the new permanent shape of the shape memory bio-based benzoxazine resin to Tg+20° C., and maintain for 40 s the cross-linked polymer will automatically return to the original shape.

Example 7

(1) Synthesis of Bio-Based Benzoxazine Monomer Containing Aldehyde Group

Furfurylamine (9.71 g) and polyformaldehyde (6.00 g) at room temperature with 15 min-stirring, followed by adding vanillin (15.22 g) to get a mixture. The mixture was heated to 90° C. and maintained at this temperature for 4 h. After that the mixture was cooled to room temperature to get a crude product, which was then recrystallized with ethanol. After the resulting pure product was dried was bio-based benzoxazine monomer containing aldehyde group.

(2) Synthesis of Schiff Base Benzoxazine Monomer

Bio-based benzoxazine monomer containing aldehyde group (37.31 g) and PEA D-230 (11.50 g, molecular weight is 230), were heated to 125° C. and stirred at this temperature for 1 h, after that the mixture was cooled to room temperature, the product was dried to obtain Schiff base benzoxazine monomer.

(3) Preparation of Benzoxazine Resin

The Schiff base benzoxazine monomer (11.0 g) was heated and degassed under vacuum at 150° C. for 10 min, and then the molten liquid was cured using the program of 160° C./1 h+180° C./1 h+200° C./1 h+220° C./1 h+240° C./1 h, the resulting cured resin was coded as shape memory bio-based benzoxazine resin.

(4) The application method of the shape memory resin bio-based benzoxazine: the sample was heated to 300° C. (Tg+20° C.), was bent into the required temporary shape with external force, and then continue heating to 300° C. and maintain at this temperature and external force, so that eversible exchange reaction of the Schiff base dynamic bond in the polymer system. Dropping to room temperature, the new shape; after that, the sample was placed in a hot air atmosphere Heating the new permanent shape of the shape memory bio-based benzoxazine resin to Tg+20° C., and maintain for 40 s the cross-linked polymer will automatically return to the original shape.

Example 8

(1) Synthesis of Bio-Based Benzoxazine Monomer Containing Aldehyde Group

Furfurylamine (9.71 g) and polyformaldehyde (6.00 g) at room temperature with 15 min-stirring, followed by adding vanillin (15.22 g) to get a mixture. The mixture was heated to 90° C. and maintained at this temperature for 5 h. After that the mixture was cooled to room temperature to get a crude product, which was then recrystallized with ethanol. After the resulting pure product was dried was bio-based benzoxazine monomer containing aldehyde group.

(2) Synthesis of Schiff Base Benzoxazine Monomer

Bio-based benzoxazine monomer containing aldehyde group (37.31 g) and PEA D-230 (11.50 g, molecular weight is 230), were heated to 125° C. and stirred at this temperature for 1 h, after that the mixture was cooled to room temperature, the product was dried to obtain Schiff base benzoxazine monomer.

(3) Preparation of Benzoxazine Resin

The Schiff base benzoxazine monomer (11.0 g) was heated and degassed under vacuum at 150° C. for 10 min, and then the molten liquid was cured using the program of 160° C./1.5 h+180° C./1.5 h+200° C./1.5 h+220° C./1.5 h+240° C./1.5 h, the resulting cured resin was coded as shape memory bio-based benzoxazine resin.

(4) The application method of the shape memory resin bio-based benzoxazine: the sample was heated to 300° C. (Tg+20° C.), was bent into the required temporary shape with external force, and then continue heating to 300° C. and maintain at this temperature and external force, so that eversible exchange reaction of the Schiff base dynamic bond in the polymer system. Dropping to room temperature, the new shape; after that, the sample was placed in a hot air atmosphere Heating the new permanent shape of the shape memory bio-based benzoxazine resin to Tg+20° C., and maintain for 40 s the cross-linked polymer will automatically return to the original shape.

Example 9

(1) Synthesis of Bio-Based Benzoxazine Monomer Containing Aldehyde Group

Furfurylamine (9.71 g) and polyformaldehyde (6.00 g) at room temperature with 15 min-stirring, followed by adding vanillin (15.22 g) to get a mixture. The mixture was heated to 85° C. and maintained at this temperature for 5 h. After that the mixture was cooled to room temperature to get a crude product, which was then recrystallized with ethanol. After the resulting pure product was dried was bio-based benzoxazine monomer containing aldehyde group.

(2) Synthesis of Schiff Base Benzoxazine Monomer

Bio-based benzoxazine monomer containing aldehyde group (30.04 g) and PEA D-230 (12.65 g, molecular weight is 230), were heated to 125° C. and stirred at this temperature for 1 h, after that the mixture was cooled to room temperature, the product was dried to obtain Schiff base benzoxazine monomer.

(3) Preparation of Benzoxazine Resin

The Schiff base benzoxazine monomer (11.0 g) was heated and degassed under vacuum at 150° C. for 10 min, and then the molten liquid was cured using the program of 150° C./2 h+170° C./2 h+190° C./2 h+210° C./2 h+240° C./2 h, the resulting cured resin was coded as shape memory bio-based benzoxazine resin.

(4) The application method of the shape memory resin bio-based benzoxazine: the sample was heated to 300° C. (Tg+20° C.), was bent into the required temporary shape with external force, and then continue heating to 300° C. and maintain at this temperature and external force, so that eversible exchange reaction of the Schiff base dynamic bond in the polymer system. Dropping to room temperature, the new shape; after that, the sample was placed in a hot air atmosphere Heating the new permanent shape of the shape memory bio-based benzoxazine resin to Tg+20° C., and maintain for 40 s the cross-linked polymer will automatically return to the original shape.

The invention discloses a shape memory bio-based benzoxazine resin, and preparation and application method thereof. Which raw materials with bio-based furfurylamine and polyformaldehyde, through heating reaction under suitable conditions, to obtain bio-based benzoxazine monomer containing aldehyde group; Through coupling reaction between bio-based benzoxazine monomer containing aldehyde group and polyetheramine to obtain Schiff base benzoxazine monomer; The Schiff base benzoxazine monomer is cured to obtain a shape memory bio-based benzoxazine resin.

The preparation process of the invention is simple, new bio-based benzoxazine monomer with Schiff base and polyether structures were synthesized using a green solvent-free strategy, the yield is high. Significantly reduces the dependence of polymer materials on fossil resources. Compared with the prior art, shape memory bio-based benzoxazine resin of the present invention has excellent thermal properties (Tg is 280° C.), high storage modulus (2.46 GPa) and tensile strength (90.4 MPa).

Shape memory bio-based benzoxazine resin by the method of the present invention, that original shape can be permanently changed requirements. It overcomes the defect that the traditional cross-linked polymer cannot be processed again after molding, thus making the polymer have the ability of shape recovery under heating stimulation conditions (above the glass transition temperature). The excellent thermal, greenization, mechanical properties and high performance requirements are greatly increasing the applicable scope of the shape memory bio-based benzoxazine resin in present invention.

The invention claimed is:

1. A method of preparing a shape memory bio-based benzoxazine resin, comprising the following steps:
   (1) heating and reacting furfurylamine, a formaldehyde compound and vanillin, recrystallizing to obtain a bio-based benzoxazine monomer containing aldehyde group;
   (2) conducting a coupling reaction of bio-based benzoxazine monomer containing aldehyde group and polyetheramine to obtain a Schiff base benzoxazine monomer; and
   (3) curing the Schiff base benzoxazine monomer to obtain the shape memory bio-based benzoxazine resin.

2. The method of claim 1, wherein the step (1) comprises: stirring a mixture of furfurylamine and the formaldehyde compound at room temperature, and adding vanillin into the mixture of furfurylamine and the formaldehyde compound; the formaldehyde compound is formaldehyde or paraformaldehyde; and a molar ratio of furfurylamine, the formaldehyde compound and vanillin is 100:(200-220):100.

3. The method of claim 1, wherein the step (1) is conducted at 80° C. to 90° C. for 4 hours to 6 hours, and the bio-based benzoxazine monomer containing aldehyde group is recrystallized in ethanol.

4. The method of claim 1, wherein in the step (2), the coupling reaction is conducted at 125° C. to 130° C. for 1 hour to 2 hours without a solvent in both synthesis and purification processes.

5. The method of claim 1, wherein in the step (2), a molar ratio of bio-based benzoxazine monomer containing aldehyde group and polyetheramine is 100:50.

6. The method of claim 1, wherein in the step (3), the Schiff base benzoxazine monomer is degassed and then cured at 150° C. to 240° C. for 10 hours to 24 hours.

7. A shape memory bio-based benzoxazine resin preparing according to the method of claim 1.

8. The method of claim 1, further comprising:
   bending the shape memory bio-based benzoxazine resin from an original shape into a changed shape and heating the shape memory bio-based benzoxazine resin at a deformation temperature;
   cooling to room temperature to obtain the shape memory bio-based benzoxazine resin with the change shape; and
   heating the shape memory bio-based benzoxazine resin with the change shape at the deformation temperature again to return the shape memory bio-based benzoxazine resin to the original shape.

9. The method of claim 8, wherein the deformation temperature ranges from Tg+10° C. to Tg+20° C., and Tg is a glass transition temperature of the shape memory bio-based benzoxazine resin.

10. The method of claim 8, wherein the shape memory bio-based benzoxazine resin is heated 290° C. to 300° C. for 20 seconds to 30 seconds.

* * * * *